United States Patent [19]
Schuller et al.

[11] 4,179,920
[45] Dec. 25, 1979

[54] CORROSION COUPON HOLDER APPARATUS

[75] Inventors: Ronald A. Schuller; Robert I. Clarkson, both of Tulsa, Okla.

[73] Assignee: Geosource, Inc., Tulsa, Okla.

[21] Appl. No.: 880,629

[22] Filed: Feb. 23, 1978

[51] Int. Cl.$^2$ ............................................ G01N 17/00
[52] U.S. Cl. ...................................................... 73/86
[58] Field of Search ............... 73/86, 422 R, 422 TC, 73/432 R; 324/65 CR, 61 P; 23/230 C; 422/53; 138/108; 137/268, 318

[56] References Cited

U.S. PATENT DOCUMENTS

| | | | |
|---|---|---|---|
| 2,783,644 | 3/1957 | Willis | 73/86 |
| 2,870,629 | 1/1959 | Willis | 73/86 |
| 2,928,726 | 3/1960 | Oberly | 73/86 X |
| 3,011,196 | 12/1961 | Glover | 137/268 X |
| 3,063,080 | 11/1962 | Bergman et al. | 137/268 X |
| 3,174,332 | 3/1965 | Echtler et al. | 73/86 |

*Primary Examiner*—Jerry W. Myracle
*Attorney, Agent, or Firm*—Cox, Smith, Smith, Hale & Guenther, Incorporated

[57] ABSTRACT

A pipeline corrosion coupon holder apparatus for large diameter pipelines which has a coupon housing assembly mounted adjacent the pipeline with the coupon housing assembly allowing access to a coupon withdrawn from the pipeline for removal and replacement of the coupon through the coupon housing assembly without removal of the coupon through a shaft housing assembly which has a reciprocally mounted shaft for insertion and retrieval of the coupon from the large diameter pipeline.

10 Claims, 10 Drawing Figures

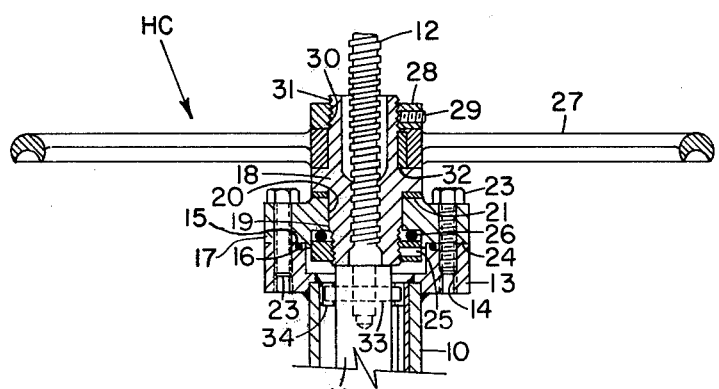
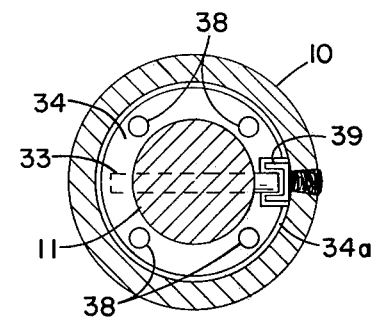
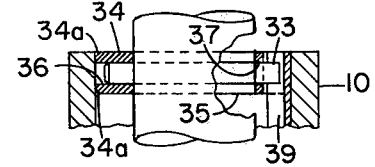
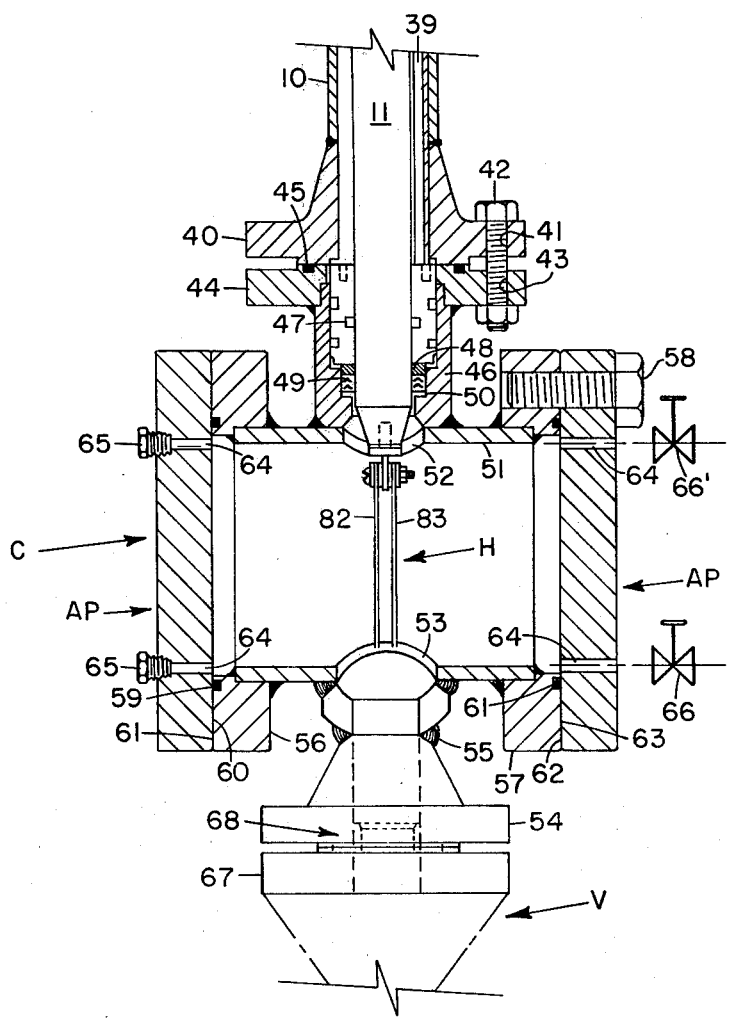
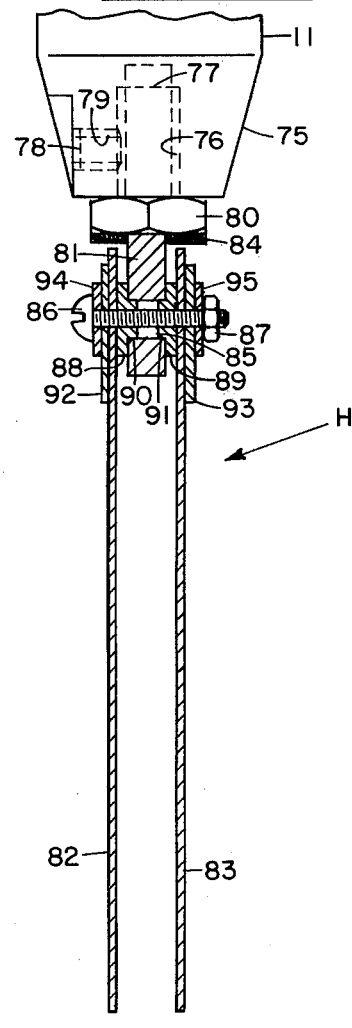

CORROSION COUPON HOLDER APPARATUS

BACKGROUND OF THE INVENTION

This invention relates generally to pipeline corrosion detecting apparatuses. More particularly, the invention relates to an apparatus for inserting and retrieving coupons from large diameter pipelines to periodically check for corrosion and wear of the pipeline due to flow of medium such as corrosive fluids or suspensions through the pipeline.

It is known in the prior art that the flow of fluids or suspensions through pipelines can result in corrosion and deterioration of the pipeline at its inner wall. Such pipelines may often be inaccesible due to being buried underground or otherwise concealed. It has been the practice to insert test coupons into the pipeline. The test coupons are constructed of a suitable material such as the pipeline itself, so that the corrosive effects on the coupon are indicative of the corrosive effects on the pipeline. In large diameter pipeline, such as 24-inch and 36-inch pipelines, the apparatus for inserting the coupon generally includes an elongated shaft housing assembly extending from the pipeline. So far as known, it has been a practice in the past to retrieve the coupon through the elongated shaft housing assembly. In the case of large diameter pipelines, this would require extended heights for removal of a shaft, which mounts coupons on one end thereof, through the shaft housing assembly. The extended height may make it difficult for a single operator to retrieve the coupons.

SUMMARY OF THE INVENTION

A new and improved pipeline corrosion coupon holder apparatus for large diameter pipelines which has a reciprocating shaft reciprocally mounted with a shaft housing assembly for insertion of the shaft into a large diameter pipeline. A coupon holder is provided on the end of the shaft which is inserted in the pipeline to insert and retrieve the coupons into the pipeline for testing of wear and corrosion of the pipeline. A coupon housing assembly is provided to mount the shaft and shaft housing assembly onto the pipeline and an access cover is provided on the coupon housing assembly to allow access to the coupons without withdrawal of the coupons and shaft through the shaft housing assembly. A full opening valve is provided between the coupon housing assembly and the pipeline to shut off the pipeline from the coupon housing assembly and suitable pressure relief valves are provided on the coupon housing assembly.

BRIEF DESCRIPTION OF THE DRAWING

FIG. 3 is an elevation view, partly in cross-section, illustrating the upper portion of the shaft housing assembly.

FIG. 4 is an elevation view, partly in section, showing the details of the coupon housing assembly.

FIG. 5 is a cross-sectional view of the shaft housing assembly taken along line 5—5 in FIG. 2A.

FIG. 6 is a elevation view, partly in section, illustrating the coupons and coupon holding portion of the retrievable shaft.

FIG. 8 is a cross-sectional view of a guide which mounts the retrievable shaft in the shaft housing assembly.

BRIEF DESCRIPTION OF THE PREFERRED EMBODIMENT

Figure 1A:
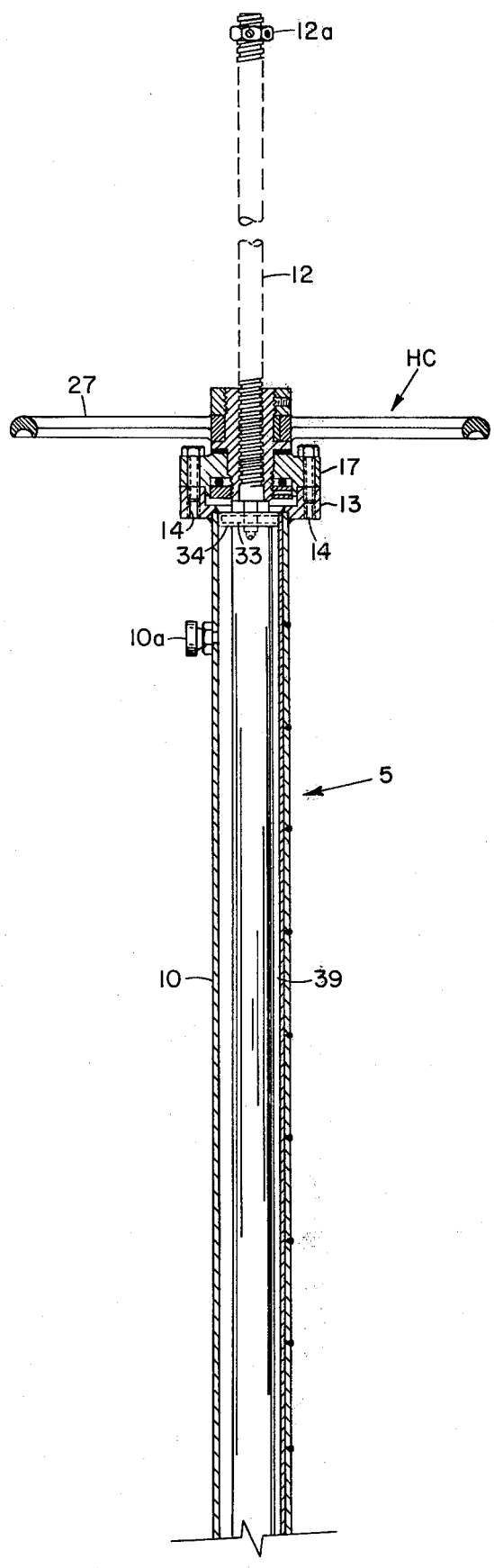
FIG. 1A is an elevation view, partly in cross-section, showing a portion of the elongated shaft housing assembly as it would appear with the coupon withdrawn from the pipeline.
Figure 1B:
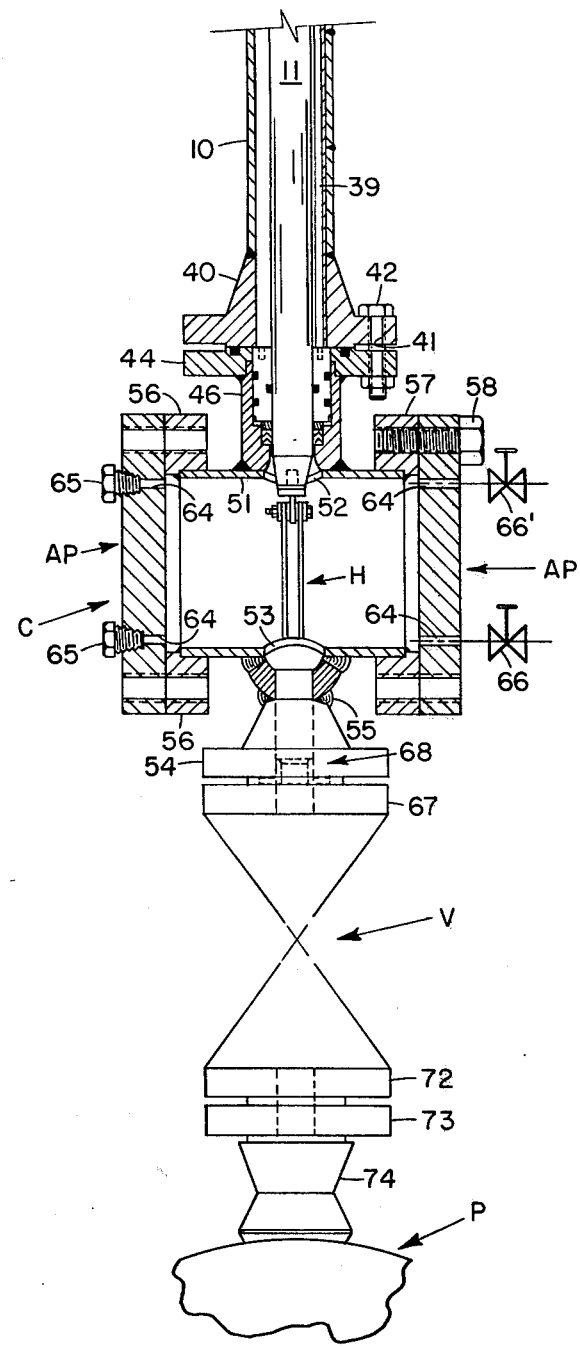
FIG. 1B is an elevation view showing the other portion of the elongated shaft housing assembly with the shaft withdrawn from the shaft housing assembly and the coupon positioned in the coupon housing assembly.
Figure 2A:
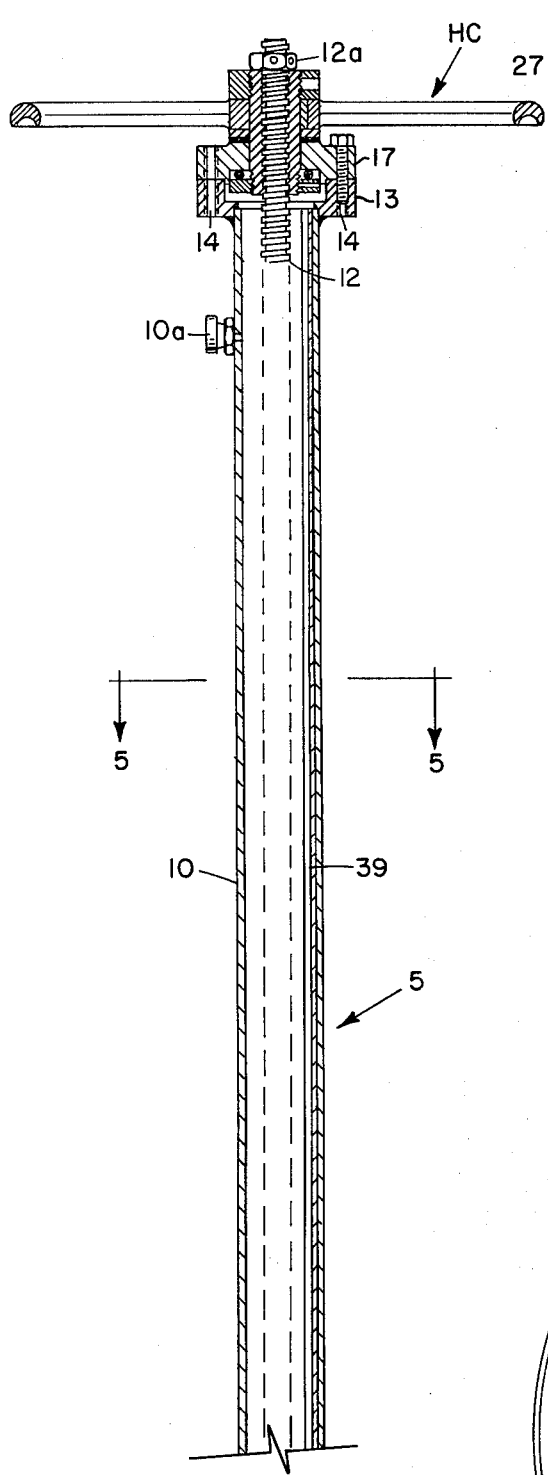
FIG. 2A is an elevation view, partly in section, illustrating a portion of the shaft housing assembly as it would appear with the coupon inserted in the pipeline.
Figure 2B:
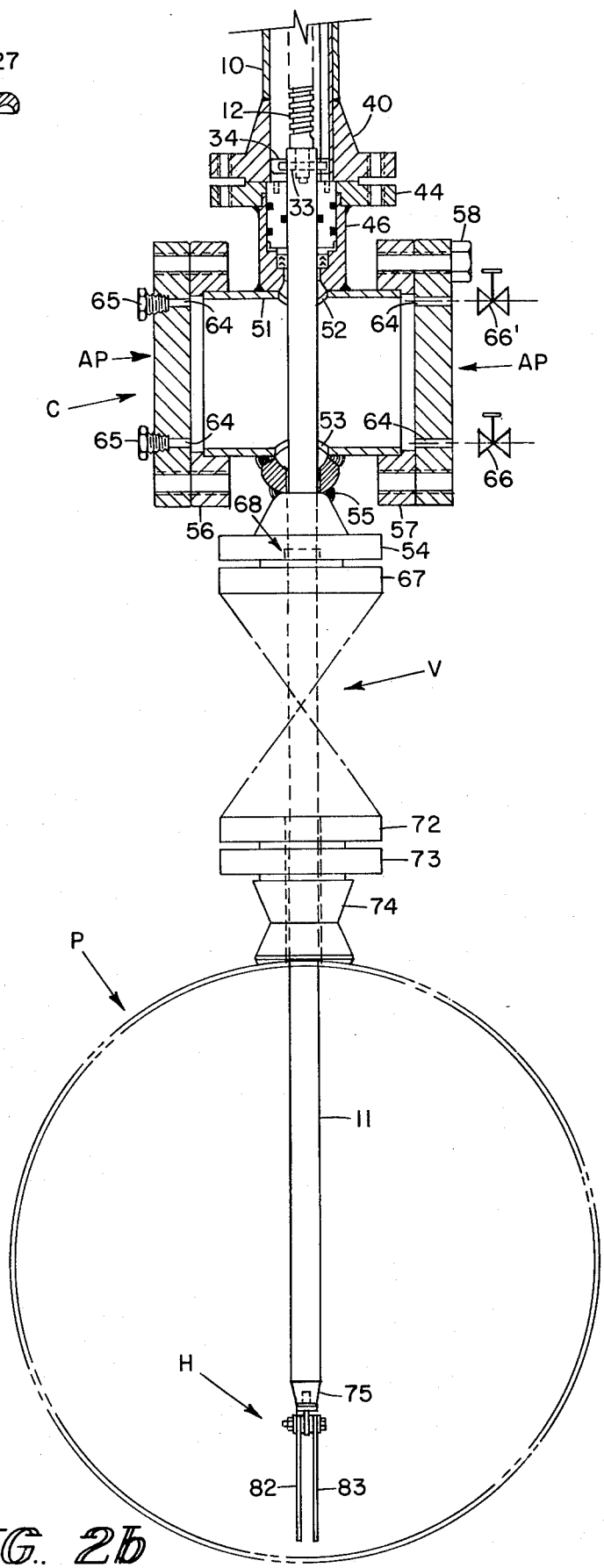
FIG. 2B is an elevation view, partly in section, of the other portion of the elongated shaft housing assembly and the coupon housing assembly with the coupon inserted within a pipeline.

The corrosion coupon holder apparatus of the invention is best shown in FIGS. 1A and 1B, and FIGS. 2A and 2B. The apparatus includes a shaft housing assembly S and a coupon housing assembly C. A coupon holder H is provided for inserting in a pipeline schematically illustrated in FIG. 2B. The operation of the device in brief includes rotating a hand wheel assembly HC to reciprocate the coupon holder H out of the pipeline P until the coupon holder is positioned within the coupon housing assembly C, as best shown in FIG. 1B and FIG. 4. An access plate AP on the coupon housing assembly C is removed to allow access to the coupon holder H for removal and testing of coupons on the holder H. The tested or new coupons may be then remounted on the coupon holder and reinserted into the pipeline, as shown in FIG. 2B. The valve V allows closing off of flow from the pipeline into the coupon housing assembly for testing of the coupons.

The shaft housing assembly S includes tubular member 10 which has mounted at its upper end the hand wheel assembly HC and at its lower end the coupon housing assembly C. A shaft 11 is mounted for reciprocating movement in the tubular member 10. At the lower end of the shaft 11 is mounted the coupon holder H. The upper portion of the shaft 11 includes threaded section 12 which is operatively connected with the hand wheel assembly HC.

The hand wheel assembly HC includes lower flange collar 13 secured with the upper end of the tubular member 10. The lower flange collar 13 includes a plurality of threaded apertures 14. An annular recess is provided in the face 15 of the lower flange collar 13 for receiving a circular O-ring. An upper flange collar 17 is provided for rotatably mounting an internally threaded member 18. The internally threaded member 18 includes a cylindrical portion 19 which is rotatably received within an opening 20 in the upper flange collar 17. A bearing washer 21 facilitates rotation of the internally threaded member 18 relative to the upper flange collar 17. A plurality of openings 22 are provided in the upper flange collar for receiving studs 23 which secure the upper and lower flange collars. An annular recess is also provided in the face 24 of the upper flange collar for receiving the O-ring 16. A thrust collar lock ring 25 is secured to the lower end of the internally threaded member or thrust collar 18. The thrust collar lock ring 25 may be threaded onto mating threads on the end of the thrust collar 18 and secured into position with a set screw. A thrust bearing 26 is provided for facilitating rotation of the thrust collar relative to the upper flange. Secured at the upper end of the thrust collar 18 is a hand wheel 27. The hand wheel 27 is secured in place with a lock ring 28 which is held in position by a set screw 29. Lock ring 28 has suitable threads 30 which mate with threads 31 on the thrust collar so that the lock ring 28 may be tightened to rigidly secure the hand wheel 27. A key 32 is provided to secure the hand wheel 27 with the thrust collar 18.

The threaded section 12 is secured with the shaft 11 by means of a guide pin 33 which inserts through a rod guide 34 and through openings in the shaft 12 and threaded section 12. Rod guide 34 and guide pin 33 are best shown in FIGS. 5 and 8. Rod guide 34 includes an inner cylindrical surface 35 which tightly fits around the shaft 11. Radial openings 36 and 37 are provided for receiving the pin 33. A plurality of axial openings 38 are provided in the rod guide 34 to allow lubricating oil, which is confined in the tubular member 10, to pass through the axial openings 38.

A U-shaped channel 39, as shown in cross-section in FIG. 5, extends the length of the tubular member 10 and receives the guide pin 33 between the legs of the U-shaped channel member. Suitable means such as welds are provided over the length of the tubular member to secure the guide channel 39 thereto. Longitudinal sliding movement of the guide pin 33 within the guide channel 39 prevents rotation of the shaft 11 and threaded section 12 relative to the tubular member 10. A flange collar 40 is secured to the lower end of the tubular member 10 by suitable means such as welding. The flange collar 40 includes a plurality of openings 41 for insertion of a plurality of bolts 42 therein. Bolts 42 extend through openings 43 and flange collar 44 to secure the flange collar 44 with the flange collar 40. A suitable seal means such as an O-ring 45 is provided to seal the mating faces of the flange collars. A breather cap 10 allows filling of oil into the tubular member.

The coupon housing assembly C includes an upper tubular member 46 which is secured with the flange collar 44 by suitable means such as welding. The tubular member 46 includes a first cylindrical opening for receiving a O-ring bushing 47 which forms a seal between the reciprocating shaft 11 and tubular member 46 through a plurality of O-rings. A follower ring 48 abuts a chevron type packing 49 which in turn abuts a retainer ring 50. The chevron type packing 49 and O-ring bushing 47 provide an additional seal so that fluids from the pipeline cannot leak into the space between the tubular member 10 and shaft 11 and also, so that oil will be retained between the space between the tubular member 10 and channel 11 for lubricating screws' threads on the threaded portion 12.

The above described shaft housing assembly S provides for reciprocating of the shaft 11 for retrieving the coupon holder from the pipeline. A nut 12a is provided at the upper end of the threaded portion 12 and said nut is securable via set screws to a predetermined position on the screw threads to determine the lowermost limit of the threaded section 12 and coupon holder 14. Accordingly, when the nut 12 engages the upper end of the thrust collar 18, this defines the lower limit of the threaded section 12 and coupon holder H.

The coupon housing assembly C includes a housing portion 51 which is secured at its upper portion to the lower end of the tubular member 46. An opening 52 at the upper portion of the housing portion 51 provides a pathway for the shaft 11 to reciprocate through. A similar opening 53 at the lower portion of the tubular housing portion 51 also facilitates the reciprocating movement of the shaft 11 and holder H. A lower flange member 54 is connected via a suitable connecting means 55, such as by welding. At each end of the tubular housing portion 51 are flange members 56 and 57 which are secured with the tubular housing portion 51 by suitable means such as welding. Access plates AP and AP' mate with the flanges 56 and 57 and are secured thereto by suitable means such as studs 58 in a conventional manner. O-ring 59 seals between the face 60 of the left access plate AP' and the face 61 of the flange 56. A similar O-ring 61 seals between the face 62 of the right access plate AP and the face 63 of the flange 57. Although only a single stud 58 is shown in the drawing, it is understood that numerous studs would be based around the circumference of the access plate, so as to provide an effective seal through the O-rings. A plurality of threaded passageways 64 are provided in the access plates AP and AP'. Suitable plugs 65 may be used to block the passage way 64 in the left access plate AP' and suitable relief valves 66 and 66' are inserted in the passage way 64 in the right hand access plate AP to relieve pressure within the tubular member 51 and drain any fluid therefrom before opening of the cover plate to provide access to the holder H, when it is in the position shown in FIGS. 1B and 4.

Figure 7:
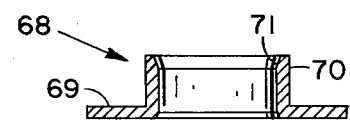
FIG. 7 is a cross-sectional view of a lower guide for the retrievable shaft.

The flange member 54 is secured to a flange 67 on the valve V. The means for securing the flanges 54 and 67 are the same as that for flanges 40 and 44. A guide bushing 68, as best shown in FIG. 7 is provided between the flanges 54 and 67 to prevent jamming of the shaft 11 and holder H there inserted through the valve V. The guide bushing 68 includes a flange sealing portion 69 and a cylindrical guide portion 70. A beveled or camming edge 71 is provided to prevent the holder H or shaft 11 from jamming on the bushing 68. The bushing 68 may be made of nylon or other suitable material.

The valve V may be of conventional construction with the primary requirement being that the valve be a full bore opening valve so as to allow passage of the holder H and shaft 11 therethrough. After the holder H is withdrawn through the valve V from the pipeline P into the coupon housing assembly C, the valve V is closed so as to prevent any further flow through the valve V into the coupon housing assembly C. The valve V includes a lower flange 72, which is mounted with a flange member 73, which flange member 73 includes a suitable connection means 74 with the pipeline P. As will be apparent, the openings in the valve flanges 67 and 72 and opening in the valve plug, as well as the opening to the connection 74 are sufficient to allow passage at the holder and shaft 11 therethrough.

The holder H is best shown in detail in FIG. 6. The lower portion of the shaft 11 is tapered at 75 which acts as a camming surface to guide and prevent jamming of the shaft 11 through the openings in the coupon housing assembly C, valve V and into the pipe P. A suitable threaded opening 76 at the lower portion of the shaft 11 is provided for receiving mated threading portion 77. A set screw 78 is received in threaded opening 79 to lock the mated threaded portion 77 in position. A tap member 80 is provided to screw the threaded portion 77 into the threaded opening 76. Lower pin member 81 is attached to the tap portion 80 and mated thread portion 77 for supporting a plurality of coupons 82 and 83. A non-conducting washer 84 is provided adjacent the tap portion 80 to prevent grounding contact of the coupons 82 and 83 with the tap portion 80. An opening 85 is provided in the pin member 81 for receiving a bolt upon which is screwed tap 87. The diameter of the threaded portion of the bolt 86 is less than the inside diameter of the opening 85 so that there is no contact between the bolt 86 and the pin member 81. The elimination of the contact is provided by the washers 88 and 89, which are made of suitable non-conducting material. The washers conclude reduced diameter portions 90 and 91 which are only slightly less in diameter than the diameter of the opening 85, so as to centrally support the bolt 86 within the opening 85 and avoid all contact of the bolt with the opening. Additional non-conducting washers 92 and 93 are provided which washers are made of non-conducting material to further insulate the coupons 82 and 83 from any conducting contact with the shaft 11. Flat washers 94 and 95 are also made of non-conducting material. As will be apparent, there is no contact between the coupons 82 and 83 with the pin 81 and in turn, the shaft 11, so as to avoid any type of cathodic reaction which might occur. Elimination of all cathodic action helps prevent the chance that corrosion of the coupons is not due to the corresponding corrosion of the pipeline.

As explained above, coupons are shown in position in the pipeline P in FIG. 2B. Fluid in the pipeline will come in contact with the coupons 82 and 83 and cause corrosion and/or wear of the coupons similar to the corrosion and/or wear to which the inner surface of the pipeline is subjected. It is understood that portions of the shaft 11 and the other components are made of relatively non-corrosive materials to avoid undesired corrosion of the apparatus. When it is desired to check the coupons, the hand wheel can be rotated to withdraw the coupons from the pipeline through the valve V and into the coupon housing assembly C. The pin 33 slides within the channel member 39 and the opening 38 in the rod guide allows the passage of oil therethrough as the rod guide 34 moves upwardly through the tubular member 10. Breather cap 10a allows air above the lubricating oil in the tubular member 10 to pass outwardly as well as providing for filling of the tubular member 10 with oil. When the coupons have reached an uppermost position, as best shown in FIGS. 1B and 4, the valve V may then be closed to prevent any further flow through the valve V into the coupon housing from the pipeline P. The valve 66 is then opened to allow relief of pressure in the coupon housing assembly C and then the valve 66' is opened to drain any fluid out of the coupon housing assembly C. The studs 58 may then be removed to remove the righthand access plate AP to provide access to the coupons 82 and 83. The tap 87 may be removed to allow removal of the bolt 86 for removal of the coupons 82 and 83 from the pin member 81. The coupons 82 and 83 or additional coupons are remounted after testing of corrosion of the coupons and the righthand access plate AP is then repositioned to seal the coupon housing assembly C. The valve V may then be opened and by turning of the hand wheel 27, the coupons are lowered back into the pipeline. The tap member 12a limits the lowermost position of the coupons 82 and 83 to a predetermined position within the pipeline P. It is understood that the valves 66 and 66' were closed after they were initially opened and prior to the opening of the valve V to insert the coupons back into the pipeline.

While there has been shown and described a preferred embodiment of a corrosion coupon holder apparatus in accordance with the invention, it will be appreciated that many changes and modification may be made therein without, however, departing from the essential spirit of the invention within the scope of the claims.

We claim:

1. A pipeline corrosion coupon holder apparatus for large diameter pipelines comprising:

an elongated shaft housing assembly for inserting and retrieving a test coupon for a large diameter pipeline for detecting corrosion and wear of the pipeline;

said shaft housing assembly having a reciprocating shaft connecting with a coupon for inserting and retrieving the coupon and further having a first securing portion;

a coupon housing assembly having a second securing portion secured with the first securing portion of the elongated shaft housing assembly to position the elongated shaft housing assembly and coupon housing assembly on the same side of the pipeline and having a third securing portion for attaching to the large diameter pipeline;

said coupon housing assembly having a removable access plate to allow access to a coupon for removal and replacement at the coupon housing assembly without removal of the coupons through the elongated shaft housing assembly and without detaching the first, second or third securing portions; and the coupon housing assembly having a guide bushing at the third securing portion to prevent jamming of the coupon during retrieving and inserting of the coupon.

2. A pipeline corrosion coupon holder apparatus for large diameter pipelines comprising:

an elongated shaft housing assembly for inserting and retrieving a test coupon for a large diameter pipeline for detecting corrosion and wear of the pipeline;

said shaft housing assembly having a reciprocating shaft connecting with a coupon for inserting and retrieving the coupon and further having a first securing portion;

a coupon housing assembly having a second securing portion secured with the first securing portion of the elongated shaft housing assembly to position the elongated shaft housing assembly and coupon housing assembly on the same side of the pipeline and having a thrid securing portion for attaching to the large diameter pipeline;

said coupon housing assembly having a removable access plate to allow access to a coupon for removal and replacement at the coupon housing assembly without removal of the coupons through the elongated shaft housing assembly and without detaching the first, second or third securing portions;

the reciprocating shaft having a guide pin; and the shaft housing having an elongated guide for movement of the guide pin therein to prevent rotation of the shaft.

3. The apparatus as set forth in claim 1 or 2, wherein: the coupon housing assembly has oppositely disposed removable access plates for removal and replacement of a coupon.

4. The apparatus as set forth in claim 1 or 2 wherein:
the coupon housing assembly has a relief valve for relieving pressure within the coupon housing assembly.

5. The apparatus as set forth in claim 1 or 2, wherein:
the reciprocating shaft has a threaded portion; and
the shaft housing assembly has a wheel assembly operatively connected with the threaded protion to reciprocate the threaded portion, and shaft for retrieving and inserting a coupon.

6. The apparatus as set forth in claim 1 or 2 wherein:
the shaft housing assembly forms an enclosure for the shaft to contain a supply of lubricating fluid surrounding the shaft.

7. The apparatus as set forth in claim 1 or 2, wherein:
the coupon housing assembly has a seal means to prevent leakage of fluid from the pipeline into the shaft housing assembly.

8. The apparatus as set forth in claim 1 or 2 wherein:
the reciprocating shaft has an upper actuating portion for causing the shaft to reciprocate and which does not pass through the coupon housing assembly and a lower portion which can be reciprocally moved through the coupon housing assembly for insertion and retrieving a coupon whereby the upper actuating portion is not subjected to the fluid from the pipeline.

9. The apparatus as set forth in claim 8, wherein:
a seal means is provided to keep the fluid from the pipeline from the upper actuating portion.

10. The apparatus as set forth in claim 8, wherein:
the upper actuating portion is a threaded portion.

* * * * *